United States Patent
Clark et al.

(10) Patent No.: US 8,217,214 B2
(45) Date of Patent: Jul. 10, 2012

(54) PROCESS FOR PREPARING ETHYLBENZENE USING VAPOR PHASE ALKYLATION AND LIQUID PHASE TRANSALKYLATION

(75) Inventors: Michael C. Clark, Chantilly, VA (US); Vijay Nanda, Houston, TX (US); Carlos N. Lopez, Amissville, VA (US); Brian Maerz, Chelmsford, MA (US); Maruti Bhandarkar, East Weymouth, MA (US)

(73) Assignees: ExxonMobil Chemical Patents Inc., Houston, TX (US); Stone & Weber, Inc., Houston, TX (US)

( * ) Notice: Subject to any disclaimer, the term of this patent is extended or adjusted under 35 U.S.C. 154(b) by 0 days.

(21) Appl. No.: 13/076,782

(22) Filed: Mar. 31, 2011

(65) Prior Publication Data

US 2011/0178352 A1 Jul. 21, 2011

Related U.S. Application Data

(60) Continuation of application No. 12/752,453, filed on Apr. 1, 2010, now Pat. No. 7,939,704, which is a division of application No. 11/805,047, filed on May 22, 2007, now abandoned.

(60) Provisional application No. 60/808,235, filed on May 24, 2006.

(51) Int. Cl.
*C07C 2/66* (2006.01)
*C07C 6/12* (2006.01)

(52) U.S. Cl. ......... 585/899; 585/323; 585/467; 585/475

(58) Field of Classification Search .................. 585/899, 585/323, 467, 475
See application file for complete search history.

(56) References Cited

U.S. PATENT DOCUMENTS

| | | |
|---|---|---|
| 3,751,504 A | 8/1973 | Keown et al. |
| 4,016,218 A | 4/1977 | Haag et al. |
| 4,547,605 A | 10/1985 | Kresge et al. |
| 4,891,458 A | 1/1990 | Innes et al. |
| 5,334,795 A | 8/1994 | Chu et al. |
| 5,557,024 A | 9/1996 | Cheng et al. |
| 5,600,048 A | 2/1997 | Cheng et al. |
| 5,900,518 A | 5/1999 | Merrill et al. |
| 5,995,642 A | 11/1999 | Hsu et al. |
| 6,897,346 B1 | 5/2005 | Merrill et al. |
| 6,984,764 B1 | 1/2006 | Roth et al. |

FOREIGN PATENT DOCUMENTS

| | | |
|---|---|---|
| WO | 94/13603 | 6/1994 |

*Primary Examiner* — Thuan Dinh Dang
(74) *Attorney, Agent, or Firm* — Darryl M. Tyus

(57) ABSTRACT

Disclosed are ethylbenzene processes in which a series-arranged or combined vapor phase alkylation/transalkylation reaction zone is retrofitted to have a vapor phase alkylation reactor and a liquid phase transalkylation reactor, and in which a parallel-arranged vapor phase alkylation reactor and vapor phase transalkylation reactor is retrofitted to have a vapor phase alkylation reactor and liquid phase transalkylation reactor, wherein the xylenes content of the ethylbenzene product is less than 700 wppm.

3 Claims, No Drawings

PROCESS FOR PREPARING ETHYLBENZENE USING VAPOR PHASE ALKYLATION AND LIQUID PHASE TRANSALKYLATION

CROSS-REFERENCE TO RELATED APPLICATIONS

This application is a continuation application of U.S. Ser. No. 12/752,453, filed Apr. 1, 2010, now U.S. Pat. No. 7,939,704, which is a divisional application of U.S. Ser. No. 11/805,047, filed May 22, 2007, now abandoned, which claims the benefit of Provisional Application No. 60/808,235, filed May 24, 2006, the disclosures of which are incorporated by reference in their entireties.

BACKGROUND OF THE INVENTION

The present invention relates to a process for preparing ethylbenzene using vapor phase alkylation and liquid phase transalkylation. One embodiment of the present invention includes an ethylbenzene process in which a series-arranged or combined vapor phase alkylation/transalkylation reaction zone is retrofitted to have a vapor phase alkylation reactor and a liquid phase transalkylation reactor. Another embodiment of the present invention includes an ethylbenzene process in which a parallel-arranged vapor phase alkylation reactor and vapor phase transalkylation reactor is retrofitted to have a vapor phase alkylation reactor and liquid phase transalkylation reactor. Still another embodiment is an apparatus for the practice of the ethylbenzene process of this invention.

Ethylbenzene is a valuable commodity chemical which is used industrially for the production of styrene monomer, most of which is used to make polystyrene. Ethylbenzene may be produced by a number of different chemical processes. One process which has achieved a significant degree of commercial success is a vapor phase ethylbenzene process in which benzene is alkylated with ethylene in the presence of an alkylation catalyst, such as solid, acidic zeolite catalyst comprised of a solid, crystalline aluminosilicate, i.e., ZSM-5 zeolite. In the first generation vapor phase ethylbenzene process, the reaction takes place in a single reactor having a series-arranged alkylation/transalkylation reaction zone that is maintained under suitable vapor phase alkylation/transalkylation conditions. Ethylbenzene is produced along with polyalkylated byproducts and xylenes byproducts. The polyalkylated byproducts are referred to as "polyethylbenzenes" when used in connection with the alkylation of benzene with ethylene, and such polyethylbenzene include diethylbenzene, triethylbenzene, tetraethylbenzene, and pentaethylbenzene and hexaethylbenzene. Ethylbenzene and a small amount of its co-boilers, such as xylene, are separated from the polyalkylated byproducts. Such ethylbenzene is typically used as styrene monomer feed. The remaining polyalkylated byproducts are recycled to the alkylation/transalkylation reaction zone.

In the second generation vapor phase ethylbenzene process, a parallel-arranged alkylation reactor and transalkylation reactor are used to produce ethylbenzene. In the alkylation reactor, benzene is alkylated with ethylene in the presence of a solid, acidic zeolite catalyst and under suitable vapor phase conditions to form ethylbenzene and polyalkylated byproducts and xylenes byproducts. Ethylbenzene and its co-boilers, such as xylene, are separated from the polyalkylated byproducts and typically used as styrene monomer feed as in the earlier process. The amount of ethylbenzene co-boilers, such as xylenes, is typically lower with such second generation vapor phase ethylbenzene processes as compared to its first generation counterparts. The second generation vapor phase process as differs from the first generation process in that the polyalkylated byproducts, such as polyethylbenzenes, are sent to a separate transalkylation reactor. In the transalkylation reaction, the polyalkylated byproducts is contacted with benzene in the presence of a transalkylation catalyst, such as solid, acidic catalyst comprised of a solid, crystalline aluminosilicate, i.e., ZSM-5 zeolite, to produce additional ethylbenzene and a reduced amount of polyalkylated byproducts.

Examples of such vapor phase ethylbenzene processes are described in U.S. Pat. Nos. 3,751,504 (Keown), 4,547,605 (Kresge) and 4,016,218 (Haag).

Another ethylbenzene process which has achieved significant commercial success is the all liquid phase process for producing ethylbenzene from benzene and ethylene. This all liquid phase process operates at a lower temperature and higher pressure than its vapor phase counterparts, but with often greater ethylbenzene capacity and lower yields of polyalkylated byproducts and xylenes byproducts, as compared to such vapor phase counterparts. For example, U.S. Pat. No. 4,891,458 (Innes) describes the liquid phase synthesis of ethylbenzene with zeolite Beta, whereas U.S. Pat. No. 5,334,795 (Chu) describes the use of MCM-22 in the liquid phase synthesis of ethylbenzene.

Even with the lower byproduct yields in the all liquid phase process for producing ethylbenzene, polyalkylated byproducts and xylenes byproducts are still inherently produced. The polyalkylated byproducts are transalkylated with additional benzene in a separate transalkylation reactor as in the second generation vapor phase processes, to produce additional ethylbenzene and a reduced amount of polyalkylated byproducts, however such transalkylation is conducted under suitable liquid phase transalkylation conditions. The amount of ethylbenzene co-boilers, such as xylenes, is typically lower with such all liquid phase ethylbenzene processes as compared to its first generation and second generation counterparts. Examples of catalysts which have been used in the all liquid phase processes for the alkylation of benzene with ethylene and for the transalkylation of polyalkylated byproducts, such as diethylbenzenes, are listed in U.S. Pat. No. 5,557,024 (Cheng) and include MCM-22, PSH-3, SSZ-25, zeolite X, zeolite Y, zeolite Beta, acid dealuminized mordenite and TEA-mordenite. Transalkylation over a small crystal (<0.5 micron) form of TEA-mordenite is also disclosed in U.S. Pat. No. 6,984,764.

The older, vapor phase ethylbenzene processes may be retrofitted to the newer, all liquid phase processes, in order to obtain the higher capacities and lower yields of the polyalkylated byproducts and xylenes byproduct. However, the cost to retrofit these older, vapor phase ethylbenzene processes to a full liquid phase process, i.e., liquid phase alkylation combined with liquid phase transalkylation, may be high. For example, to retrofit certain first generation, vapor phase ethylbenzene processes (series-arranged alkylation/transalkylation reaction zones in a single reactor) to full liquid phase processes, a new transalkylation reactor must be installed and the single must be converted from combined alkylation and transalkylation service to only alkylation service. Also, high capacity transfer pumps must be installed to maintain gaseous ethylene in the liquid phase with benzene.

Similarly, to retrofit certain second generation vapor phase ethylbenzene process (parallel-arranged alkylation and transalkylation reactors) to a full liquid phase process, for example, both the alkylation and transalkylation reactors must be converted from vapor phase service to liquid phase service. In some retrofits, the size of the reactors must be increased. As in retrofitting the first generation vapor phase processes, high capacity transfer pumps must be installed to maintain gaseous ethylene in the liquid phase with benzene.

The costs to retrofit older, vapor phase ethylbenzene processes to the newer, full liquid phase processes, having higher capacity and lower polyalkylated byproduct yields, has proven to be a significant deterrent. Efforts have been made to revamp older, ethylbenzene processes having a vapor phase alkylation reactors and vapor phase translation reactors, such as in second generation ethylbenzene processes, by converting the vapor phase alkylation reactor to a liquid phase alkylation reactors, while maintaining the transalkylation reactor in the vapor phase.

In U.S. Pat. No. 5,600,048 (Cheng), a continuous process for preparing ethylbenzene using liquid phase alkylation and vapor phase transalkylation is disclosed. The liquid phase alkylation reaction may be catalyzed by an acidic solid oxide, such as MCM-22, MCM-49 and MCM-56. The vapor phase transalkylation may be catalyzed by a medium-pore size zeolite such as ZSM-5. The process may be run continuously with the continuous introduction of fresh benzene feed containing at least 500 wppm of nonbenzene hydrocarbon impurities. The combined ethylbenzene product of these alkylation and transalkylation reactions has very low levels of impurities including xylene, hydrocarbons having 7 or less carbon atoms and hydrocarbons having 9 or more carbon atoms.

U.S. Pat. No. 5,995,642 (Merrill) discloses an alkylation/transalkylation process involving vapor phase alkylation of a benzene feedstock in a multi-stage alkylation zone having a plurality of series connected catalyst beds containing a pentasil aromatic alkylation catalyst, such as silicalite, coupled with intermediate separation and recirculation steps and liquid phase transalkylation over a transalkylation catalyst comprising a molecular sieve having a pore size greater than the pore size of the silicalite. The benzene containing feedstock is supplied to the multi-stage alkylation reaction zone along with a $C_2$-$C_4$ alkylating agent operated under temperature and pressure conditions to maintain the benzene in the gas phase. Alkylated product is recovered from the alkylation zone and supplied to a benzene recovery zone for the separation of the benzene from the alkylation product. Benzene from the benzene recovery zone is recycled to the reaction zone. A higher boiling bottom fraction containing a mixture of monoalkylated and polyalkylated aromatic components is supplied to a secondary separation zone from which a monoalkylated aromatic component, e.g. ethylbenzene, is recovered overhead with a heavier polyalkylated aromatic recovered as a bottom fraction. The bottom fraction may be applied to a tertiary separation zone.

U.S. Pat. No. 6,897,346 (Merrill) discloses a process for the transalkylation of polyalkylated aromatic compounds over a high porosity zeolite-Y molecular sieve having a surface area of no more than 500 m$^2$/g. A feedstock comprising a polyalkylated aromatic component, including polyalkylbenzenes in which the predominant alkyl substituents contain from 2 to 4 carbon atoms, is supplied to a transalkylation reaction zone containing the high porosity zeolite-Y catalyst. Benzene is also supplied to the transalkylation zone, and the reaction zone is operated under temperature and pressure conditions to maintain the polyalkylated aromatic component in the liquid phase and which are effective to cause disproportionation of the polyalkylated aromatic component to arrive a disproportionation product having a reduced polyalkylbenzene content and an enhanced monoalkylbenzene content. An alkylation reaction zone is provided which contains a molecular sieve aromatic alkylation catalyst having an average pore size which is less than the average pore size of the average pore size of the high porosity zeolite-Y. A feedstock comprising benzene in a $C_2$-$C_4$ alkylating agent is supplied to the alkylation reaction zone which is operated under conditions to produce alkylation of the benzene by the alkylating agent in the presence of the molecular sieve alkylation catalyst. The alkylation product from the alkylation reaction zone is supplied to an intermediate recovery zone for the separation and recovery of a monoalkylbenzene, e.g. ethylbenzene, from the alkylation product; together with the recovery of a polyalkylated aromatic component employing a dialkylbenzene, e.g. diethylbenzene. The polyalkylated aromatic component is employed in at least a portion of the feedstream supplied to the transalkylation reactor.

WO 94/13603 (Abichandani et al.) discloses a process for producing ethylbenzene, wherein benzene is alkylated with ethylene in a vapor phase reaction over a catalyst comprising ZSM-5. Diethylbenzene byproduct from the vapor phase alkylation reaction is separated from the ethylbenzene product and reacted with benzene in a liquid phase transalkylation reaction to produce more ethylbenzene. The catalyst for the liquid phase transalkylation reaction may comprise a zeolite, such as zeolite beta. The combined ethylbenzene product from the vapor phase alkylation reaction and from the liquid phase transalkylation reaction has a low xylene impurities level of less than 1000 ppm.

None of these prior art process teaches an ethylbenzene process having a vapor phase alkylation reactor combined with a liquid phase transalkylation reactor, wherein the combined ethylbenzene product from the vapor phase alkylation reaction and from the liquid phase transalkylation reaction has a low xylene impurities level of less than 700 wppm. Therefore, there is a need for such ethylbenzene processes.

According to the present invention, it has now unexpectedly been found that older, vapor phase ethylbenzene process may be successfully retrofitted to an improved process that combines vapor phase alkylation with liquid phase transalkylation, wherein such improved process has higher ethylbenzene capacity and lower yields of polyalkylated byproduct and xylenes byproduct as compared to an all vapor phase ethylbenzene process. In first generation, vapor phase ethylbenzene processes, for example, the single reactor having series-arranged alkylation and transalkylation zones is converted to alkylation service and a liquid phase transalkylation reactor is installed. In second generation, vapor phase ethylbenzene processes, for example, the transalkylation reactor is converted to liquid phase and the vapor phase alkylation reaction is substantially unmodified. In both such examples, the addition of larger transfer pumps is minimized. More importantly, in both such vapor phase ethylbenzene processes, the concomitant benefits of increased ethylbenzene capacity and a lower xylenes byproduct yields may be realized.

SUMMARY OF THE INVENTION

According to one embodiment of the present invention, there is provided a process for preparing ethylbenzene, said process comprising the steps of:
(a) contacting an alkylation feed which comprised benzene and ethylene in the presence of an alkylation catalyst in an alkylation reaction zone, to generate an alkylation product which comprises ethylbenzene, xylenes, and polyethylbenzene, said alkylation reaction zone is operated under suitable vapor phase alkylation conditions to maintain substantially all of said alkylation feed and said alkylation product in the vapor phase;

(b) separating a polyethylbenzene product from at least a portion of said alkylation product;
(c) contacting a transalkylation feed which comprises said polyethylbenzene product and benzene in the presence of a transalkylation catalyst in a transalkylation reaction zone, to generate a transalkylation product which comprises ethylbenzene and xylenes, said transalkylation reaction zone is operated under suitable liquid phase transalkylation conditions to maintain substantially all of said transalkylation feed and said transalkylation product in the liquid phase;
(d) separating an ethylbenzene product from a crude product stream which comprises said transalkylation product and said remaining portion of said alkylation product; and
wherein the xylenes content of said ethylbenzene product is less than about 700 wppm, preferably, less than about 600 wppm, most preferably, less than about 500 wppm.

The alkylation catalyst for the vapor phase alkylation of benzene with ethylene of this invention comprises a solid, crystalline aluminosilicate selected from the group consisting of ZSM-5, ZSM-11, ZSM-12, ZSM-22, ZSM-23, ZSM-35, ZSM-48, ZSM-50 and mixtures thereof. Preferably, the alkylation catalyst comprises ZSM-5, more preferably, the alkylation catalyst comprises at least 70 wt. % ZSM-5.

The transalkylation catalyst for the liquid phase transalkylation of polyethylbenzenes with benzene of this invention comprises a solid, crystalline aluminosilicate selected from the group consisting of zeolite Beta, zeolite Y, mordenite, TEA-mordenite, MCM-22, PSH-3, SSZ-25, ERB-1, ITQ-1, ITQ-2, ITQ-30, MCM-36, MCM-49, MCM-56 and mixtures thereof. Preferably, the transalkylation catalyst includes zeolite Y, mordenite, or TEA-mordenite.

Another embodiment of the present invention is an improved process for the production of ethylbenzene which comprises the steps of contacting a benzene feed, an ethylene feed and a polyethylbenzene feed in the presence of an alkylation catalyst in an alkylation reactor, to generate an alkylation product which comprises ethylbenzene and xylenes, said alkylation reactor is operated under suitable vapor phase alkylation conditions to maintain substantially all of said feeds and said alkylation product in the vapor phase, separating from said alkylation product a first ethylbenzene product having a first xylenes content, the improvement comprising the steps of:
(a) providing to said process a transalkylation reactor having a transalkylation catalyst;
(b) removing said polyethylbenzene feed from said alkylation reactor and supplying said polyethylbenzene feed to said transalkylation reactor;
(c) contacting said polyethylbenzene feed with benzene in the presence of said transalkylation catalyst in said transalkylation reactor, to generate a transalkylation product which comprises ethylbenzene and xylenes, said transalkylation reactor is operated under suitable liquid phase transalkylation conditions to maintain substantially all of said polyalkylated product, said benzene and said transalkylation product in the liquid phase;
(d) separating said transalkylation product to generate a second ethylbenzene product; and
wherein the sum of the amount of said first ethylbenzene product and the amount of second ethylbenzene product is at least 10 percent greater than, more preferably at least 15 percent greater than, and most preferably at least 20 percent greater that the amount of said first ethylbenzene product.

Still another embodiment of the present invention is an improved process for the production of ethylbenzene which comprises the steps of contacting an alkylation feed which comprises benzene and ethylene in the presence of an alkylation catalyst in an alkylation reactor, to generate an alkylation product which comprises ethylbenzene, xylenes and polyethylbenzenes, said alkylation reactor operated under suitable vapor phase alkylation conditions to maintain substantially all of said alkylation feed and said alkylation product in the vapor phase, separating a first ethylbenzene product and a polyethylbenzene product from at least a portion of said alkylation product, contacting a transalkylation feed which comprises said polyethylbenzene product and benzene in the presence of a vapor phase transalkylation catalyst in a transalkylation reactor operated under suitable vapor phase transalkylation conditions to maintain substantially all of said transalkylation feed and said transalkylation product in the vapor phase, to generate a first transalkylation product which comprises ethylbenzene and xylenes, separating said first transalkylation product to generate a second ethylbenzene product, the improvement comprising the steps of:
(a) removing said vapor phase transalkylation catalyst from said transalkylation reactor;
(b) supplying said transalkylation reactor with a liquid phase transalkylation catalyst;
(c) operating said transalkylation reactor under suitable liquid phase transalkylation conditions to maintain substantially all of said transalkylation feed and said transalkylation product in the liquid phase, to generate a second transalkylation product which comprises ethylbenzene and xylenes;
(d) separating a third ethylbenzene product from said second transalkylation product; and
wherein the sum of the amount of said first ethylbenzene product and the amount of said third ethylbenzene product is at least 10 percent greater than, preferably at least 15 percent greater than, and most preferably at least 20 percent greater than the sum of the amount of said first ethylbenzene product and the amount of said second ethylbenzene product.

Still yet another embodiment of the present invention is an apparatus for the production of ethylbenzene, comprising:
(a) an alkylation reactor having at least one alkylation inlet, at least one alkylation reaction zone and at least one alkylation outlet, said alkylation inlet adapted to introduce at least one alkylation feed stream into said alkylation reaction zone, said alkylation feed stream comprising at least ethylene and at least benzene, said alkylation reaction zone having at least one alkylation catalyst and adapted to maintain suitable vapor phase alkylation conditions, wherein at least one alkylation effluent may be produced when said alkylating agent and said alkylatable aromatic compound are contacted in the presence of said alkylation catalyst, said alkylation effluent which comprises said ethylbenzene and polyethylbenzenes, said alkylation outlet adapted to remove said alkylation effluent;
(b) a means for separating said polyethylbenzenes from at least a portion of said alkylation effluent;
(c) a transalkylation reactor having at least one transalkylation inlet, at least one transalkylation reaction zone and at least one transalkylation outlet, said transalkylation inlet adapted to introduce at least one transalkylation feed stream into said transalkylation reaction zone, said transalkylation feed stream which comprises said polyethylbenzene and benzene, said transalkylation reaction zone having a transalkylation catalyst and adapted to maintain suitable liquid phase transalkylation conditions, wherein at least one transalkylation effluent may be produced when said transalkylation feed stream are contacted in the presence of said transalkylation catalyst, said transalkylation effluent which comprises additional ethylbenzene and a reduced amount of polyalkylated aromatic compounds, said transalkylation outlet adapted to remove said transalkylation effluent;

(d) a means for separating said ethylbenzene product from a crude product stream which comprises said remaining portion of said alkylation effluent and said transalkylation effluent, said ethylbenzene product which comprises ethylbenzene and xylenes; and wherein the xylenes content of said ethylbenzene product is less than about 700 wppm, preferably less than about 600 wppm, and most preferably less than about 500 wppm.

DETAILED DESCRIPTION OF THE INVENTION

In the current commercial processes for preparing ethylbenzene, both the alkylation reaction and the transalkylation reaction typically take place in the same phase, i.e., either both in the vapor phase or both in the liquid phase. In the vapor phase commercial process, higher temperatures are required to maintain vapor phase conditions. At the temperatures employed in these vapor phase conditions, considerable quantities of xylene impurities are formed. Since the boiling point for xylenes is very close to the boiling point for ethylbenzene, the ethylbenzene product from such an all vapor phase process exceeds 700 wppm of xylene impurities. Earlier vapor phase ethylbenzene process, such as the Mobil/Badger process, may produce an ethylbenzene product having 1200-1600 wppm of xylene byproducts. These xylene byproducts, which coboil with ethylbenzene, may contaminate downstream products derived from ethylbenzene, such as styrene and polystyrene.

The lower operating temperature required for the all liquid phase process typically produces less than 100 wppm xylene byproducts.

The present invention is a process for preparing ethylbenzene from benzene and ethylene in which a vapor phase alkylation reactor is combined with a liquid phase transalkylation reactor. In one embodiment, there is provided a process for preparing ethylbenzene, said process comprising the steps of:

(a) contacting an alkylation feed which comprised benzene and ethylene in the presence of an alkylation catalyst in an alkylation reaction zone, to generate an alkylation product which comprises ethylbenzene, xylenes, and polyethylbenzene, said alkylation reaction zone is operated under suitable vapor phase alkylation conditions to maintain substantially all of said alkylation feed and said alkylation product in the vapor phase;

(b) separating a polyethylbenzene product from at least a portion of said alkylation product;

(c) contacting a transalkylation feed which comprises said polyethylbenzene product and benzene in the presence of a transalkylation catalyst in a transalkylation reaction zone, to generate a transalkylation product which comprises ethylbenzene and xylenes, said transalkylation reaction zone is operated under suitable liquid phase transalkylation conditions to maintain substantially all of said transalkylation feed and said transalkylation product in the liquid phase;

(d) separating an ethylbenzene product from a crude product stream which comprises said transalkylation product and said remaining portion of said alkylation product; and wherein the xylenes content of said ethylbenzene product is less than about 700 wppm, preferably, less than about 600 wppm, most preferably, less than about 500 wppm.

In another embodiment of this invention, a first generation vapor phase ethylbenzene process is retrofitted such that the series-connected, combined alkylation and transalkylation reactor is converted to a vapor phase alkylation reactor and a new, separate, liquid phase transalkylation reactor is installed. The retrofitted vapor phase alkylation reactor and new liquid phase transalkylation reactor may be operated at lower severity and higher weight hourly space velocity (by increased ethylene throughput and lower benzene-to-ethylene feed ratios) as compared to its first generation counterpart. The lower severity conditions, such as reduced temperature, for example, produces a lower yield of the undesirable xylene byproduct and a lower yield of the polyethylbenzene byproduct. The new liquid phase transalkylation reactor also produces a lower yield of the undesirable xylene byproduct due to its lower severity operating conditions, as compared to the first generation, transalkylation reaction zone.

As used herein, the terms "retrofit" means to install new or modified process equipment, such as reactors, conduits, pumps, and the like to previously constructed equipment.

In this retrofit, this improved process for the production of ethylbenzene which comprises the steps of contacting a benzene feed, an ethylene feed and a polyethylbenzene feed in the presence of an alkylation catalyst in an alkylation reactor, to generate an alkylation product which comprises ethylbenzene and xylenes, said alkylation reactor is operated under suitable vapor phase alkylation conditions to maintain substantially all of said feeds and said alkylation product in the vapor phase, separating from said alkylation product a first ethylbenzene product having a first xylenes content, the improvement comprising the steps of:

(a) providing to said process a transalkylation reactor having a transalkylation catalyst;

(b) removing said polyethylbenzene feed from said alkylation reactor and supplying said polyethylbenzene feed to said transalkylation reactor;

(c) contacting said polyethylbenzene feed with benzene in the presence of said transalkylation catalyst in said transalkylation reactor, to generate a transalkylation product which comprises ethylbenzene and xylenes, said transalkylation reactor is operated under suitable liquid phase transalkylation conditions to maintain substantially all of said polyalkylated product, said benzene and said transalkylation product in the liquid phase;

(d) separating said transalkylation product to generate a second ethylbenzene product; and wherein the sum of the amount of said first ethylbenzene product and the amount of second ethylbenzene product is at least 10 percent greater than, more preferably at least 15 percent greater than, and most preferably at least 20 percent greater that the amount of said first ethylbenzene product.

In still another embodiment of this invention, a second generation, vapor phase ethylbenzene process is retrofitted in which the vapor phase alkylation reactor is maintained, while the parallel-connected vapor phase transalkylation reactor is converted to liquid phase. In this retrofit, both the vapor phase alkylation reactor and the liquid transalkylation reactor may be operated at lower severity as compared to its second generation counterpart. The lower severity conditions, such as reduced temperature, for example, produces a lower yield of the undesirable xylene byproduct and a lower yield of the polyethylbenzene byproduct. Also, both the vapor phase alkylation reactor and the liquid transalkylation reactor may have higher weight hourly space velocity by increased ethylene throughput and lower benzene-to-ethylene feed ratios) as compared to the second generation counterpart.

In this retrofit, the improved process for the production of ethylbenzene which comprises the steps of contacting an alkylation feed which comprises benzene and ethylene in the presence of an alkylation catalyst in an alkylation reactor, to generate an alkylation product which comprises ethylbenzene, xylenes and polyethylbenzenes, said alkylation reactor operated under suitable vapor phase alkylation conditions to maintain substantially all of said alkylation feed and said alkylation product in the vapor phase, separating a first ethylbenzene product and a polyethylbenzene product from at least a portion of said alkylation product, contacting a transalkylation feed which comprises said polyethylbenzene product and benzene in the presence of a vapor phase transalkylation catalyst in a transalkylation reactor operated under suitable vapor phase transalkylation conditions to maintain substantially all of said transalkylation feed and said transalkylation product in the vapor phase, to generate a first transalkylation product which comprises ethylbenzene and xylenes, separating said first transalkylation product to generate a second ethylbenzene product, the improvement comprising the steps of:

(a) removing said vapor phase transalkylation catalyst from said transalkylation reactor;
(b) supplying said transalkylation reactor with a liquid phase transalkylation catalyst;
(c) operating said transalkylation reactor under suitable liquid phase transalkylation conditions to maintain substantially all of said transalkylation feed and said transalkylation product in the liquid phase, to generate a second transalkylation product which comprises ethylbenzene and xylenes;
(d) separating a third ethylbenzene product from said second transalkylation product; and wherein the sum of the amount of said first ethylbenzene product and the amount of said third ethylbenzene product is at least 10 percent greater than, preferably at least 15 percent greater than, and most preferably at least 20 percent greater than the sum of the amount of said first ethylbenzene product and the amount of said second ethylbenzene product.

In still yet another embodiment, this invention includes an apparatus for the production of ethylbenzene, comprising:

(a) an alkylation reactor having at least one alkylation inlet, at least one alkylation reaction zone and at least one alkylation outlet, said alkylation inlet adapted to introduce at least one alkylation feed stream into said alkylation reaction zone, said alkylation feed stream comprising at least ethylene and at least benzene, said alkylation reaction zone having at least one alkylation catalyst and adapted to maintain suitable vapor phase alkylation conditions, wherein at least one alkylation effluent may be produced when said alkylating agent and said alkylatable aromatic compound are contacted in the presence of said alkylation catalyst, said alkylation effluent which comprises said ethylbenzene and polyethylbenzenes, said alkylation outlet adapted to remove said alkylation effluent;
(b) a means for separating said polyethylbenzenes from at least a portion of said alkylation effluent;
(c) a transalkylation reactor having at least one transalkylation inlet, at least one transalkylation reaction zone and at least one transalkylation outlet, said transalkylation inlet adapted to introduce at least one transalkylation feed stream into said transalkylation reaction zone, said transalkylation feed stream which comprises said polyethylbenzene and benzene, said transalkylation reaction zone having a transalkylation catalyst and adapted to maintain suitable liquid phase transalkylation conditions, wherein at least one transalkylation effluent may be produced when said transalkylation feed stream are contacted in the presence of said transalkylation catalyst, said transalkylation effluent which comprises additional ethylbenzene and a reduced amount of polyalkylated aromatic compounds, said transalkylation outlet adapted to remove said transalkylation effluent;
(d) a means for separating said ethylbenzene product from a crude product stream which comprises said remaining portion of said alkylation effluent and said transalkylation effluent, said ethylbenzene product which comprises ethylbenzene and xylenes; and wherein the xylenes content of said ethylbenzene product of said ethylbenzene product is less than about 700 wppm, preferably less than about 600 wppm, and most preferably less than about 500 wppm.

The weight ratio of xylenes to ethylbenzene of the ethylbenzene product produced by the instant ethylbenzene processes of this invention which has a vapor phase alkylation reactor and a liquid phase transalkylation reactor is less than 700 wppm, preferably less than 600 wppm, and most preferably less than 500 wppm.

Alkylation and/or Transalkylation Conditions

The increase in ethylbenzene capacity of the instant ethylbenzene processes of this invention which has a vapor phase alkylation reactor and a liquid phase transalkylation reactor is at least 10 percent greater than, more preferably at least 15 percent greater than, and most preferably at least 20 percent greater than the ethylbenzene capacity of first generation or second generation vapor phase ethylbenzene counterparts.

When benzene is alkylated with ethylene to produce ethylbenzene, the alkylation reaction is carried out under vapor phase alkylation conditions which include a temperature of about 300 to 500° C., preferably from about 650 to 900° F. (343 to 482° C.), e.g., from about 700 to 850° F. (371 to 454° C.), a pressure of 100 to 20790 kPa-a (14.7 to 3015 psia), preferably from about 273.6 kPa-a (25 psig) to about 3202 kPa-a (450 psig), a weight hourly space velocity (WHSV) based on ethylene of about 0.5 to about 10.0 hr$^{-1}$, e.g., about 0.5 to about 2.0 hr$^{-1}$, and a molar ratio of benzene to ethylene of about 1:1 to 30:1.

When polyethylbenzene is transalkylated with benzene to produce ethylbenzene and a reduced polyethylbenzene content, the transalkylation reaction may be carried out under vapor phase transalkylation conditions which include a temperature of about 300 to 500° C., a pressure of 100 to 20790 kPa-a (14.7 to 3015 psia), a weight hourly space velocity (WHSV) based on the polyethylbenzenes of about 0.5 to 100 hr.$^{-1}$, and a weight ratio of benzene to polyethylbenzene from 1:1 to 10:1.

When polyethylbenzene is transalkylated with benzene to produce ethylbenzene and a reduced polyethylbenzene content, the transalkylation reaction may also be carried out under liquid phase transalkylation conditions which include a temperature of 100 to 300° C. a pressure of 690 to 4135 kPa-a (100 to 600 psia), a weight hourly space velocity based on polyethylbenzene product (WHSV) of 0.1 to 100 hr$^{-1}$, and a weight ratio of benzene to polyethylbenzene product of 0.5:1 to 10:1.

In the alkylation of benzene with ethylene to produce ethylbenzene, the alkylation reactor effluent contains ethylbenzene, excess benzene and polyethylbenzene byproducts and other various impurities. The excess benzene feed is recovered in a benzene distillation column and recycled to the alkylation reactor. Usually a small bleed is taken from the recycle stream to eliminate unreactive impurities from the loop. The bottoms from the benzene distillation column may be further distilled to the ethylbenzene product from polyethylbenzene products and other heavies.

The polyethylbenzene products separated from the alkylation reactor effluent may be reacted with additional benzene feed in a transalkylation reactor, separate from the alkylation reactor, over a suitable transalkylation catalyst. The transalkylation reactor may be operated under liquid phase conditions Alkylation Catalyst The vapor phase alkylation catalysts that may be used in the present invention may comprise one or more solid, crystalline aluminosilicate materials or molecular sieves selected from the group consisting of ZSM-5, ZSM-11, ZSM-12, ZSM-22, ZSM-23, ZSM-35, ZSM-48, ZSM-50 and mixtures thereof.

In some embodiments of this disclosure, the alkylation catalyst used in the present invention comprises the zeolite ZSM-5 having a crystal size (maximum dimension in any direction) of no greater than 0.1 micron, e.g., about 0.02 to about 0.08 micron, alternatively from about 0.02 to about 0.05 micron. ZSM-5 is disclosed in U.S. Pat. No. 3,702,886 and U.S. Pat. Reissue No. 29,948 and a process for making small crystal ZSM-5 is disclosed in U.S. Pat. No. 4,060,568, U.S. Pat. No. 5,240,892 and U.S. Pat. No. 5,369,071.

The alkylation catalyst may include the solid, crystalline material or molecular sieve in unbound or self-bound form or, alternatively, the material or molecular sieve can be combined in a conventional manner with an oxide binder as hereinafter detailed. The catalyst for use in the present invention may include an inorganic oxide material matrix or binder. Such matrix materials include synthetic or naturally occurring substances as well as inorganic materials such as clay, alumina, silica and/or metal oxides. The latter may be either naturally occurring or in the form of gelatinous precipitates or gels including mixtures of silica and metal oxides. Naturally occurring clays which can be composited with the inorganic oxide material include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. In some preferred embodiments of this disclosure, the alkylation catalyst contains at least 70 wt. % zeolite, more preferably 70-90 wt. %, and most preferably 75-85 wt. % zeolite, for example about 80 wt. % zeolite.

Specific useful catalyst matrix or binder materials employed herein include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

In a preferred embodiment, the zeolite is composited with a silica binder, preferably such that the alkylation catalyst contains at least 70 wt. % zeolite, more preferably 70-90 wt. %, and most preferably 75-85 wt. % zeolite, for example about 80 wt. % zeolite.

The ZSM-5 employed preferably has a $SiO_2/Al_2O_3$ molar ratio greater than 40, more preferably from 55 to 80, and most preferably from 55 to 75.

In other embodiments of this disclosure, the alkylation catalyst comprises a silica-bound ZSM-5. A silica-bound ZSM-5 zeolite alkylation catalyst, wherein the ZSM-5 has a crystal size of no greater than, 0.1 micron, e.g., 0.02 to 0.05 micron. Preferably, the catalyst contains at least 70 wt. % zeolite. The resultant product contains both the desired monoalkylated aromatic compound and polyalkylated aromatic compounds rich in the para-dialkylaromatic species. The polyalkylated aromatic compounds are separated from the alkylation product and reacted with further aromatic feedstock in the presence of a transalkylation catalyst to produce additional monoalkylated product.

Although it is known that zeolite catalysts can be selectivated by treatment with selectivating agents such as coke or organosilicon compounds, it is preferred that the alkylation catalysts employed in the present invention not be so treated. In particular, it is preferred that the ZSM-5 catalyst employed in the alkylation step of the invention has a Diffusion Parameter, $D/(r^2 \times 10^6)$, for 2,2-dimethylbutane of at least 500, and more preferably from 700 to 2000, when measured at a temperature of 120° C. and a 2,2-dimethylbutane pressure of 60 torr (8 kPa), wherein D is the diffusion coefficient ($cm^2$/sec) and r is the crystal radius (cm). The required Diffusion Parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1957.

The process of the present invention, which employs silica-bound ZSM-5 zeolite catalyst composite of no greater than 0.1 micron, e.g., 0.02-0.08 micron, zeolite crystal size, as the alkylation catalyst, provides certain advantages over prior art processes. In particular, the polyalkylated fraction of the alkylation product contains at least 40 wt. % of the para-dialkylaromatic species. Moreover, the para-diethylbenzene content of the alkylation product is greater than 45 wt. %, preferably greater than 50 wt. % of the total diethylbenzene in the product. The high para-diethylbenzene content facilitates subsequent transalkylation.

Furthermore, the alkylation step of the process of the invention may be effected at a start of cycle temperature 20-30° F. lower, e.g., well below 750° F., than conventional vapor phase EB processes. The lower start of cycle temperature provides longer cycle lengths and higher activity.

Moreover, the silica-bound ZSM-5 used as the alkylation catalyst in the process of the invention provides lower xylene make, with the xylene content of the alkylation product typically being no greater than 900 wppm, preferably no greater than 800 wppm. In particular, the process of the present invention can provide ethylene conversion of at least 96 wt. %, preferably at least 96.5 wt % and less than 800 wppm xylenes/EB, preferably less than 750 wppm xylenes/EB, after 4 days on stream at ethylene WHSV of 4, aromatics/ethylene ratio of 50 and inlet temperatures of 750° F. Furthermore, residue production can be limited by using the present process which can provide an ethylbenzene-rich product stream containing no greater than 0.4 wt. %, preferably no greater than 0.3, wt. % $C_{11}$+ residue.

ZSM-5 is described in greater detail in U.S. Pat. Nos. 3,702,886 and Re. 29,948. The entire descriptions contained within those patents, particularly the X-ray diffraction pattern of therein disclosed ZSM-5, are incorporated herein by reference.

ZSM-11 is described in greater detail in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-22 is described in U.S. Pat. No. 4,556,477, the entire contents of which is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,406,859. The description of that zeolite, and particularly the specified X-ray diffraction pattern thereof, is incorporated herein by reference.

ZSM-48 is more particularly described in U.S. Pat. No. 4,234,231, the entire contents of which is incorporated herein by reference.

ZSM-50 is more particularly described in U.S. Application Ser. No. 705,822, filed Feb. 26, 1985, the entire disclosure of which is expressly incorporated herein by reference.

Transalkylation Catalyst

The vapor phase transalkylation catalysts for use in the present invention may comprise one or more solid, crystalline aluminosilicate materials or molecular sieves selected from the group consisting of zeolite ZSM-5, ZSM-11, ZSM-12, ZSM-22, ZSM-23, ZSM-35, ZSM-48, ZSM-50 and mixtures thereof.

The liquid phase transalkylation catalysts for use in the present invention may comprise one or more solid, crystalline aluminosilicate materials or molecular sieves selected from the group consisting of zeolite Beta, zeolite Y, mordenite, TEA-mordenite, MCM-22, PSH-3, SSZ-25, ERB-1, ITQ-1, ITQ-2, ITQ-30, MCM-36, MCM-49, MCM-56 and mixtures thereof.

Zeolite Beta is disclosed in U.S. Pat. No. 3,308,069. Zeolite Y and mordenite occur naturally but may also be used in one of their synthetic forms, such as Ultrastable Y (USY), which is disclosed in U.S. Pat. No. 3,449,070, Rare earth exchanged Y (REY), which is disclosed in U.S. Pat. No. 4,415,438, and TEA-mordenite (i.e., synthetic mordenite prepared from a reaction mixture comprising a tetraethylammonium directing agent), which is disclosed in U.S. Pat. Nos. 3,766,093 and 3,894,104. However, in the case of TEA-mordenite for use in the transalkylation catalyst, the particular synthesis regimes described in the patents noted lead to the production of a mordenite product composed of predominantly large crystals with a size greater than 1 micron and typically around 5 to 10 micron. It has been found that controlling the synthesis so that the resultant TEA-mordenite has an average crystal size of less than 0.5 micron results in a transalkylation catalyst with materially enhanced activity for liquid phase aromatics transalkylation.

The small crystal TEA-mordenite desired for transalkylation can be produced by crystallization from a synthesis mixture having a molar composition within the following ranges:

|  |  | Useful | Preferred |
|---|---|---|---|
| $R/R + Na^+$ | = | >0.4 | 0.45-0.7 |
| $OH^-/SiO_2$ | = | <0.22 | 0.05-0.2 |
| $Si/Al_2$ | = | >30-90 | 35-50 |
| $H_2O/OH$ | = | 50-70 | 50-60 |

The crystallization is conducted at a temperature of 90 to 200° C., for a time of 6 to 180 hours.

MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in U.S. Pat. No. 6,231,751), ITQ-30 (described in WO 2005-118476), MCM-36 (described in U.S. Pat. No. 5,250,277), MCM-49 (described in U.S. Pat. No. 5,236,575) and MCM-56 (described in U.S. Pat. No. 5,362,697).

The transalkylation catalyst may include the solid, crystalline material or molecular sieve in unbound or self-bound form or, alternatively, the material or molecular sieve can be combined in a conventional manner with an oxide binder as hereinafter detailed. The catalyst for use in the present invention may include an inorganic oxide material matrix or binder. Such matrix materials include synthetic or naturally occurring substances as well as inorganic materials such as clay, alumina, silica and/or metal oxides. The latter may be either naturally occurring or in the form of gelatinous precipitates or gels including mixtures of silica and metal oxides. Naturally occurring clays which can be composited with the inorganic oxide material include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

Specific useful catalyst matrix or binder materials employed herein include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of the acidic, porous crystalline materials or molecular sieve and binder or matrix in the transalkylation catalyst, if present, may vary widely with the crystalline material or molecular sieve content ranging from about 1 to about 99 percent by weight, and more usually in the range of about 30 to about 80 percent by weight of the total catalyst. Of course, the catalyst may comprise a self-bound material or molecular sieve or an unbound material or molecular sieve, thereby being about 100% acidic, porous crystalline material or molecular sieve.

The catalyst for use in the present invention, or its acidic, porous crystalline material or molecular sieve component, may or may not contain added functionalization, such as, for example, a metal of Group VI (e.g. Cr and Mo), Group VII (e.g. Mn and Re) or Group VIII (e.g. Co, Ni, Pd and Pt), or phosphorus.

All patents, patent applications, test procedures, priority documents, articles, publications, manuals, and other documents cited herein are fully incorporated by reference for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. In a retrofit of a vapor phase process for the production of ethylbenzene such that a series-connected, combined alkylation and transalkylation reactor is converted to a vapor phase alkylation reactor and a separate liquid phase transalkylation reactor in which said retrofitted process comprises the steps of (1) contacting a benzene feed, an ethylene feed and a polyethylbenzene feed in the presence of an a combined alkylation and transalkylation catalyst in said combined alkylation and transalkylation reactor, to generate an alkylation product which comprises ethylbenzene and xylenes, said combined alkylation and transalkylation reactor is operated under suitable vapor phase alkylation conditions at a first temperature and a weight hourly space velocity of ethylene, to maintain substantially all of said feeds and said alkylation product in the vapor phase, and (2) separating from said alkylation product a first ethylbenzene product having a first xylenes content greater than 700 ppm, the improvement to said process comprising the steps of:
   (a) providing to said retrofitted process said transalkylation reactor having a transalkylation catalyst;
   (b) removing said polyethylbenzene feed from said retrofitted combined alkylation and transalkylation reactor;
   (c) supplying said polyethylbenzene feed to said transalkylation reactor;
   (d) contacting said polyethylbenzene feed with benzene in the presence of said transalkylation catalyst in said transalkylation reactor, to generate a transalkylation product which comprises ethylbenzene and xylenes, said transalkylation reactor is operated under suitable liquid phase transalkylation conditions at a second temperature to maintain substantially all of said polyethylbenzene feed, said benzene and said transalkylation product in the liquid phase, wherein said second temperature is less than said first temperature;
   (e) separating said transalkylation product to generate a second ethylbenzene product having a second xylene content of less than 100 ppm; and
   wherein said weight hourly space velocity of ethylene is increased and the sum of the
   amount of said first ethylbenzene product and the amount of second ethylbenzene product is at least 15 percent greater than the amount of said first ethylbenzene product, and wherein said retrofitted alkylation and transalkylation catalyst comprises a solid, crystalline aluminosilicate selected from the group consisting of ZSM-5, ZSM-11, ZSM-12, ZSM-22, ZSM-23, ZSM-35, ZSM-48, ZSM-50 and mixtures thereof; and said retrofitted transalkylation catalyst comprises a solid, crystalline aluminosilicate selected from the group consisting of zeolite Beta, zeolite Y, mordenite, TEA-mordenite, MCM-22, PSH-3, SSZ-25, ERB-1, ITQ-1, ITQ-2, ITQ-30, MCM-36, MCM-49, MCM-56 and mixtures thereof.

2. The process of claim 1, wherein said vapor phase retrofitted alkylation conditions include a temperature of about 300 to 500° C., a pressure of 100 to 20790 kPa-a (14.7 to 3015 psia), a weight hourly space velocity (WHSV) based on ethylene of about 0.5 to about 10.0 hr$^{-1}$, and a molar ratio of benzene to ethylene of about 1:1 to 30:1.

3. The process of claim 1, wherein said liquid phase retrofitted transalkylation conditions include a temperature of 100 to 300° C. a pressure of 690 to 4135 kPa-a (100 to 600 psia), a weight hourly space velocity based on polyethylbenzene feed (WHSV) of 0.1 to 100 hr.$^{-1}$, and a weight ratio of benzene to polyethylbenzene feed of 0.5:1 to 10:1.

* * * * *